United States Patent
Portney

(10) Patent No.: US 6,557,998 B2
(45) Date of Patent: *May 6, 2003

(54) MULTIFOCAL OPHTHALMIC LENS WITH REDUCED HALO SIZE

(75) Inventor: Valdemar Portney, Tustin, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/171,723

(22) Filed: Jun. 14, 2002

(65) Prior Publication Data

US 2002/0149743 A1 Oct. 17, 2002

Related U.S. Application Data

(63) Continuation of application No. 09/758,850, filed on Jan. 11, 2001, now Pat. No. 6,435,681, which is a continuation of application No. 09/244,709, filed on Feb. 4, 1999, now Pat. No. 6,210,005.

(51) Int. Cl.$^7$ ............................ G02C 7/06; A61F 2/16
(52) U.S. Cl. ............................ 351/168; 623/6.28
(58) Field of Search ................. 351/168, 169, 351/161, 171; 623/6.11, 6.24, 6.27–6.28

(56) References Cited

U.S. PATENT DOCUMENTS

| | | | |
|---|---|---|---|
| 1,483,509 A | 2/1924 | Bugbee | 65/39 |
| 2,129,305 A | 9/1938 | Feinbloom | 351/162 |
| 2,274,142 A | 2/1942 | Houchin | 351/171 |
| 2,405,989 A | 8/1946 | Beach | 351/169 |
| 2,511,517 A | 6/1950 | Spiegel | 65/136.4 |
| 3,031,927 A | 5/1962 | Wesley | 351/161 |
| 3,034,403 A | 5/1962 | Neefe | 351/162 |
| RE25,286 E | 11/1962 | Carle | 351/161 |
| 3,210,894 A | 10/1965 | Bentley et al. | 451/42 |
| 3,227,507 A | 1/1966 | Feinbloom | 351/160 R |
| 3,339,997 A | 9/1967 | Wesley | 351/161 |

(List continued on next page.)

FOREIGN PATENT DOCUMENTS

| | | |
|---|---|---|
| DE | 2702117 | 7/1978 |
| DE | 3246306 | 6/1984 |
| EP | 0064812 | 11/1982 |
| EP | 0351471 | 1/1990 |
| EP | 0566170 | 10/1993 |
| EP | 756189 | 1/1997 |
| GB | 2058391 | 4/1981 |
| GB | 2129155 | 5/1984 |
| GB | 2146791 | 4/1985 |
| GB | 2192291 | 1/1988 |
| WO | 8603961 | 7/1986 |
| WO | 8700299 | 1/1987 |
| WO | 8707496 | 12/1987 |
| WO | 8911672 | 11/1989 |

OTHER PUBLICATIONS

Kingslake, Academic Press, 1978 pp. 36–38.
Holladay et al, J. Cataract Refr. Surg, vol. 14, 1/88 pp. 17–23.
Cohen, Rep. of South Africa Patent Application No. 888414, Nov. 10, 1988.
Contact Lens Practice, 1998, p. 211, 212, 403, 404, 491 & 792.
Encylopedia of Contact Lens Practice, Sep. 1, 1960, p. 24–26.
"The Shah Biofocal Intraocular Lens Implant", Shah & Shah Int. Lens Labs, Calcutta, India.

*Primary Examiner*—Jordan M. Schwartz
(74) *Attorney, Agent, or Firm*—Stout, Uxa, Buyan & Mullins, LLP; Frank J. Uxa; Peter Jon Gluck

(57) ABSTRACT

Ophthalmic lenses, for example, intraocular lenses, contact lenses, corneal implant lenses and the like, have multifocal characteristics which provide beneficial reductions in at least the perception of one or more night time visual symptoms such as "halos", and "glare or flare".

10 Claims, 4 Drawing Sheets

U.S. PATENT DOCUMENTS

| | | | |
|---|---|---|---|
| 3,420,006 A | 1/1969 | Barnett | 451/283 |
| 3,431,327 A | 3/1969 | Tsuetaki | 264/1.8 |
| 3,482,906 A | 12/1969 | Volk | 351/160 R |
| 3,932,148 A | 1/1976 | Krewalk, Sr. | 451/42 |
| 4,055,378 A | 10/1977 | Feneberg et al. | 351/160 R |
| 4,062,629 A | 12/1977 | Winthrop | 351/169 |
| 4,162,122 A | 7/1979 | Cohen | 351/161 |
| 4,195,919 A | 4/1980 | Shelton | 351/160 R |
| 4,199,231 A | 4/1980 | Evans | 351/160 H |
| 4,210,391 A | 7/1980 | Cohen | 351/161 |
| 4,240,719 A | 12/1980 | Guilino et al. | 351/169 |
| 4,274,717 A | 6/1981 | Davenport | 351/169 |
| 4,307,945 A | 12/1981 | Kitchen et al. | 351/169 |
| 4,315,673 A | 2/1982 | Guilino et al. | 351/169 |
| 4,338,005 A | 7/1982 | Cohen | 351/161 |
| 4,340,283 A | 7/1982 | Cohen | 351/161 |
| 4,377,329 A | 3/1983 | Poler | 351/160 R |
| 4,402,579 A | 9/1983 | Poler | 351/160 R |
| 4,418,991 A | 12/1983 | Breger | 351/161 |
| 4,504,982 A | 3/1985 | Burk | 623/6.23 |
| 4,573,775 A | 3/1986 | Bayshore | 351/161 |
| 4,580,882 A | 4/1986 | Nuchman et al. | 351/161 |
| 4,596,578 A | 6/1986 | Kelman | 623/6.17 |
| 4,618,228 A | 10/1986 | Baron et al. | 351/161 |
| 4,618,229 A | 10/1986 | Jacobstein et al. | 351/161 |
| 4,636,049 A | 1/1987 | Blaker | 351/161 |
| 4,636,211 A | 1/1987 | Nielsen et al. | 623/6.28 |
| 4,637,697 A | 1/1987 | Freeman | 351/161 |
| 4,641,934 A | 2/1987 | Freeman | 351/159 |
| 4,693,572 A | 9/1987 | Tsuetaki et al. | 351/161 |
| 4,704,016 A | 11/1987 | De Carle | 351/161 |
| 4,720,286 A | 1/1988 | Bailey et al. | 623/6.13 |
| 4,752,123 A | 6/1988 | Blaker | 351/161 |
| 4,759,762 A | 7/1988 | Grendahl | 623/6.27 |
| 4,769,033 A | 9/1988 | Nordan | 623/6.24 |
| 4,813,955 A | 3/1989 | Achatz et al. | 623/6.17 |
| 4,830,481 A | 5/1989 | Futhey et al. | 351/161 |
| 4,881,804 A | 11/1989 | Cohen | 351/161 |
| 4,890,912 A | 1/1990 | Visser | 351/161 |
| 4,890,913 A | 1/1990 | De Carle | 351/161 |
| 4,898,461 A | 2/1990 | Portney | 351/169 |
| 4,917,681 A | 4/1990 | Nordan | 623/6.24 |
| 4,919,663 A | 4/1990 | Grendahl | 623/6.28 |
| 4,923,296 A | 5/1990 | Erickson | 351/161 |
| 4,938,583 A | 7/1990 | Miller | 351/161 |
| 5,000,559 A | 3/1991 | Takahashi et al. | 351/169 |
| 5,002,382 A | 3/1991 | Seidner | 351/161 |
| 5,019,099 A | 5/1991 | Nordan | 623/6.24 |
| 5,166,711 A | 11/1992 | Portney | 351/161 |
| 5,166,712 A | 11/1992 | Portney | 351/161 |
| 5,173,723 A | 12/1992 | Volk | 351/161 |
| 5,192,317 A | 3/1993 | Kalb | 623/6.28 |
| 5,192,318 A | 3/1993 | Schneider et al. | 623/6.28 |
| 5,225,858 A | 7/1993 | Portney | 351/161 |
| 5,270,744 A | 12/1993 | Portney | 351/161 |
| 5,541,678 A | 7/1996 | Awanahara et al. | 351/161 |
| 5,691,797 A | 11/1997 | Seidner et al. | 351/161 |
| 5,805,260 A | 9/1998 | Roffman et al. | 351/161 |
| 6,210,005 B1 | 4/2001 | Portney | 351/161 |
| 6,435,681 B2 * | 8/2002 | Portney | 351/161 |

* cited by examiner

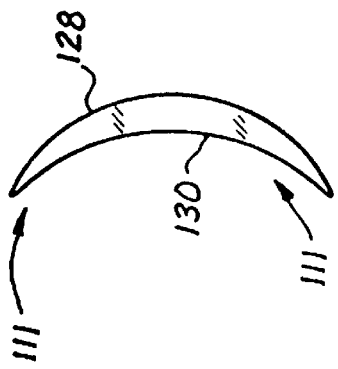
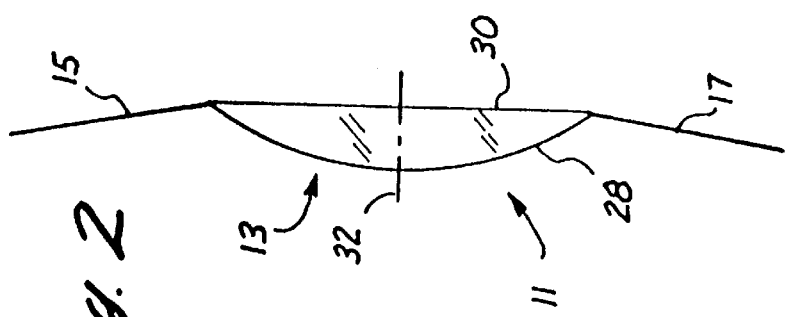
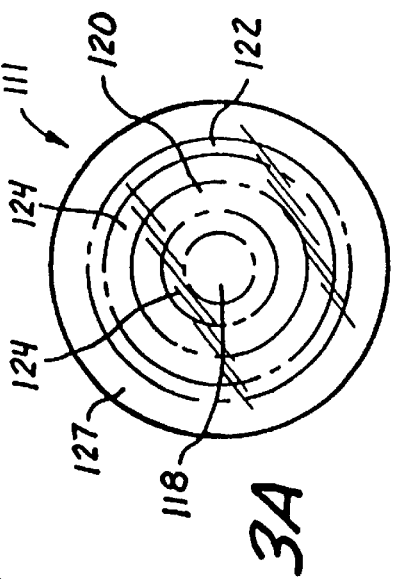
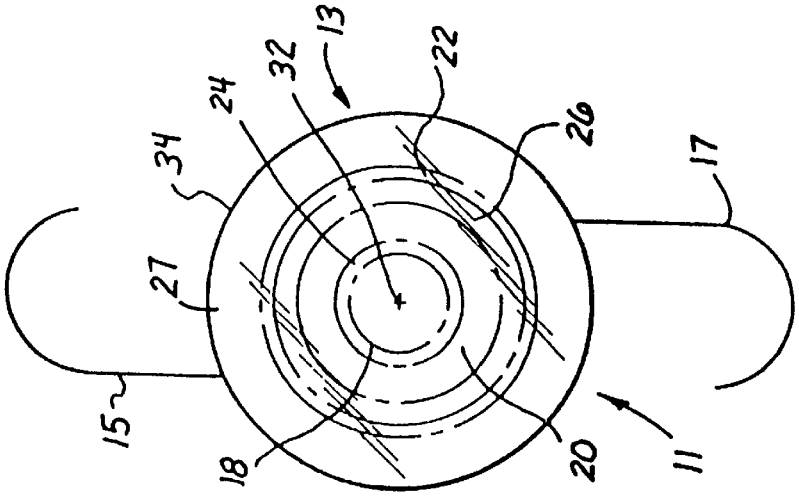
Fig. 3
Fig. 3A
Fig. 2
Fig. 1

DISTANCE FROM LENS CENTER

MULTIFOCAL OPHTHALMIC LENS WITH REDUCED HALO SIZE

This is a Ser. No. 09/758,850, filed Jan. 11, 2001, now U.S. Pat. No. 6,435,681 which, in turn, is a continuation of application Ser. No. 09/244,709, filed Feb. 4, 1999, now U.S. Pat. No. 6,210,005 B1. The disclosure of each of the above-noted applications and patent is incorporated in its entirety herein by reference.

BACKGROUND OF THE INVENTION

The present invention relates to ophthalmic lenses. More particularly, the invention relates to multifocal ophthalmic lenses for use in or on the eye, such as intraocular lenses, contact lenses, corneal implant lenses and the like.

The general construction of a multifocal ophthalmic lens is known in the art. For example, Portney U.S. Pat. 5,225,858, which is incorporated herein by reference, discloses a multifocal ophthalmic lens including a central zone circumscribed by multiple concentric, annular zones. This patent discloses multifocal lenses having good image quality and light intensity for near objects. The multifocal lens of this patent includes zones for near vision correction in which the vision correction power is substantially constant throughout.

Although multifocal lenses of this type provide very effective vision correction, further enhancements would be advantageous.

For example, experience with multifocal lenses as described above has identified two general types of night time visual symptoms referred to as "glare or flare" and "halos". The "glare or flare" symptom manifests itself as radial lines radiating from distant small bright objects at night. The "halos" symptom generally manifest itself as diffuse shadows surrounding distant small bright objects, again noticed at night. These visual symptoms are likely caused by out of focus light passing through the near zone or zones of the lenses.

SUMMARY OF THE INVENTION

New ophthalmic lenses which address one or more the above-noted symptoms have been discovered. The present lenses take advantage of the discovery that one or more modifications to the surface of a multifocal lens can provide a beneficial reduction in at least the perception of one or more of the above-noted night time visual symptoms. These modifications can be very conveniently and effectively implemented substantially without increasing the cost or difficulty of manufacturing such lenses. The present lenses preferably reduce the size of the major halo which may be apparent when viewing distant objects at night time. In addition, the central zone of the present lenses preferably is modified to change the vision correction is power above the baseline diopter power toward the center of the lens to provide an increase in ray density which enhances near image performance. In summary, the present modification or modifications to the multifocal lenses provide additional advantages in already effective multifocal ophthalmic lenses.

In one broad aspect of the present invention, an ophthalmical lens having a baseline diopter power for far vision correction is provided. The ophthalmic lens comprises a near zone, preferably an annular near zone, including an inner region, having a substantially constant vision correction power greater than the baseline diopter power and having vision correction powers greater than the baseline diopter power which reduce the size, that is the apparent or perceived size, of a halo caused by passing light to the near zone relative to the halo caused by passing light to a similar near zone of a substantially identical lens in which the similar near power has a constant vision correction power throughout.

Preferably, the near zone has a highest vision correction power, which may be the substantially constant vision correction power of the inner region, and includes an outer region located outwardly of the inner region. This outer region has vision correction powers which are progressively reduced from the highest vision correction power of the near zone to a reduced near vision correction power which is between about 50% and about 85% of the highest vision correction power of the near zone. The inner region has an innermost end and the outer region has an outermost end. The radial width of the inner region more preferably is in the range of about 30% to about 85% of the radial distance between the innermost end of the inner region and the outermost end of the outer region.

Without wishing to limit the invention to any particular theory of operation, it is believed that the reduction of the vision correction power in the outer region of the near zone is effective to reduce the size of the most apparent or most perceived halo around small light sources viewed from a distance, for example, at night time.

In one very useful embodiment, the present ophthalmic lenses further comprise an additional near zone, preferably an annular additional near zone, located outwardly of, and preferably circumscribing, the near zone and having vision correction powers greater than the baseline diopter power. The additional near zone preferably includes vision correction powers which diffuse, or increase the apparent or perceived size of, a halo caused by passing light to the additional near zone relative to the halo caused by passing light to a similar additional near zone of a substantially identical lens in which the similar additional near zone has a constant vision correction power throughout.

In one very useful embodiment, the width of the additional near zone is less than about 40% of the radial width of the near zone. The additional near zone has an inner end and an outer end and vision correction powers which preferably increase progressively from the inner end to the outer end.

The present ophthalmic lenses preferably reduce the size of the halo resulting from passing light to the near zone and increase the size of the halo resulting from passing light to the additional near zone. The overall effect of the near zone, and preferably the additional near zone, of the present ophthalmic lenses preferably is to effectively and advantageously reduce the apparent or perceived "halo" visual symptom, and more preferably the "glare or flare" visual symptom, which have been noted during use of previous multifocal lenses.

The present ophthalmic lenses preferably are selected from intraocular lenses, contact lenses, corneal implant lenses and the like.

The present ophthalmic lenses may, and preferably do, include a central zone having a vision correction power greater than the baseline diopter power. The near zone is located outwardly of, and preferably circumscribes, the central zone.

In an additional broad aspect of the present invention, ophthalmic lenses having a baseline diopter power for far vision correction are provided which comprise a central zone including a center region, an intermediate region, and an outer region. The center region has a vision correction power, for example, substantially equal to the baseline diopter power, although the center region can have a vision correction power which is less than or greater than the baseline diopter power. The intermediate region is located outwardly of the center region and has a vision correction power which is highest vision correction power in the central zone. The outer region is located outwardly of the intermediate region and has a vision correction power equal to the vision correction power of the center region. The highest vision correction power in the central zone is closer, in terms of radial distance, to the vision correction power of the center region than to the vision correction power of the outer region equal to the vision correction power of the center region.

Without wishing to limit the invention to any particular theory of operation, it is believed that the modification in which the highest vision correction power of the central zone is closer to the vision correction power of the center region increases the ray density closer to the center or optical axis of the lens, which enhances near image performance.

The vision correction powers of the central zone preferably vary progressively. The highest vision correction power in the central zone preferably is located about 40% or less, more preferably about 35% or less, of the distance, for example, the radial distance, between the vision correction power of the center region and the vision correction of the outer region equal to the vision correction power of the center region.

In one very useful embodiment, the ophthalmic lenses preferably further comprise a first outer zone located outwardly of the central zone and having a vision correction power less than the baseline diopter power; and a second outer zone located outwardly of the first outer zone and having a vision correction power greater than the baseline diopter power. Preferably, the intermediate region, the outer region, the first outer zone and the second outer zone are annular and circumscribe the center region, the intermediate region, the outer region and the first outer zone, respectively.

The second outer zone preferably includes vision correction powers which reduce the size of a halo caused by passing light to the second outer zone relative to the halo caused by passing light to a similar second outer zone of a substantially identical lens in which the similar second outer zone has a constant vision correction power throughout. The second outer zone preferably has inner and outer regions and other characteristics similar to those of the near zone described elsewhere herein.

The present ophthalmic lenses preferably include a third outer zone located outwardly of the second outer zone and having a vision correction power greater than the baseline diopter power. This third outer zone preferably includes vision correction powers which diffuse a halo caused by passing light through the third outer zone relative to the halo caused by passing light to a similar third outer zone of a substantially identical lens in which the similar third outer zone has a width which preferably is less than about 40% of the width of the second outer zone. The third outer zone preferably has an inner end and an outer end and vision correction powers which increase progressively from the inner end to the outer end.

In a very useful embodiment, the ophthalmic lenses of the present invention further comprise a fourth outer zone located outwardly of the second outer zone and inwardly of the third outer zone and having vision correction powers less than the baseline diopter power. This fourth outer zone preferably has an inner region having a vision correction power, an intermediate region located outwardly of the inner region and an outer region located outwardly of the intermediate region. The intermediate region has a vision correction power which is increased relative to the vision correction power of the inner region and is the highest vision correction power in the intermediate zone and an outermost diopter power equal to the vision correction power of the inner region. The outer region has a vision correction power which is the lowest vision correction power of the fourth outer zone. The highest vision correction power of the fourth outer zone is located closer, that is radially closer, to the vision correction power of the inner region than to the outermost vision correction power of the intermediate region. This preferred fourth outer zone configuration provides the present lenses with enhanced far vision performance, particularly in dim light and/or at night time.

The first, second and third outer zones preferably are annular and the first annular zone circumscribes the central zone, the second outer zone circumscribes the first outer zone and the third outer zone circumscribes the second outer zone. In the event the fourth outer zone is included, the fourth outer zone preferably is annular and circumscribes the second outer zone and is circumscribed by the third outer zone.

The portions of the present lenses between the various zones of differing vision correction powers can be referred to as transition Portions or zones. Such transition portions or zones can provide for an abrupt or "step function" charge in vision correction power. Preferably, however, the transition portions or zones provide for a more gradual or progressive change in vision correction power.

The desired powers for the present lenses can be provided in various different ways, including the use of refracting surfaces. In one preferred embodiment, the lens has anterior and posterior surfaces, at least one of which is shaped to provide the desired vision correction powers. With this construction, the progressive portion or portions of the lens are aspheric, and although the regions of the lens of constant power can be spheric if desired, preferably they are also aspheric. In a preferred construction, the lenses of the invention are aspheric throughout the annular zones and the central zone, and this provides certain advantages in designing the lens and also can be used to compensate for spherical aberrations for far vision portions and near vision portions of the lens.

For a contact lens, it is preferred to shape the posterior surface to fit the curvature of the patient's eye and to configure the anterior surface to provide the desired correction.

Each and every feature described herein, and each and every combination of two or more of such features are included with the scope of the present invention provided that the features included in any such combination are not mutually inconsistent.

These and other aspects of the present invention are apparent in the following detailed description and claims particularly when considered in conjunction with the accompanying drawings in which like parts bear like reference numerals.

BRIEF DESCRIPTION OF THE DRAWINGS

FIG. 1 is a plan view of a multifocal intraocular lens embodying features of this invention.

FIG. 2 is a side elevation view of the IOL shown in FIG. 1.

FIG. 3 is a side elevation view of a corneal contact lens embodying features of the present invention.

FIG. 3A is a plan view of the corneal contact lens shown in FIG. 3.

DESCRIPTION OF THE PREFERRED EMBODIMENTS

Figure 4:
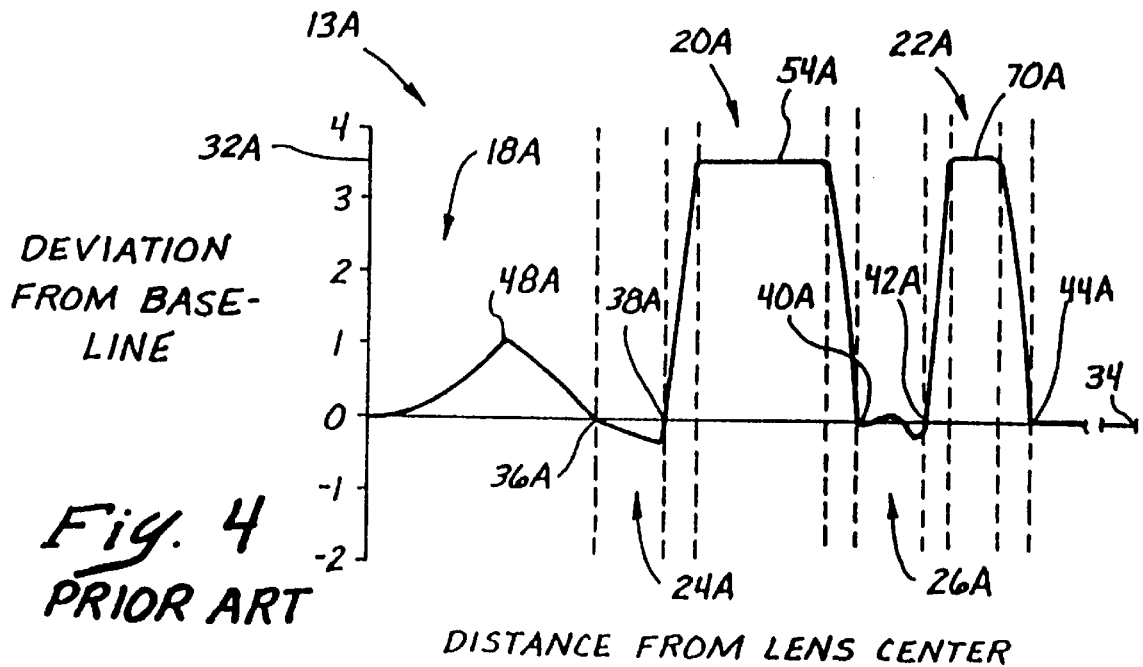
FIG. 4 is a plot of the power of an optic versus distance from the optical axis for a prior art multifocal intraocular lens.

FIGS. 1 and 2 show an intraocular lens 11 which comprises a circular optic 13 and fixation members 15 and 17. The optic 13 may be constructed of rigid biocompatible materials, such as polymehtylmethacrylate (PMMA), or flexible, deformable materials, such as silicones, deformable acrylic polymeric materials, hydrogels and the like which enable the optic to be rolled or folded for insertion through a small incision into the eye.

In this embodiment, the fixation members 15 and 17 are fine hair-like strands or filaments which are attached to the optic 13 using conventional techniques. The fixation members 15 and 17 may be constructed of a suitable polymeric material, such as PMMA or polypropylene. Alternatively, the fixation members 15 and 17 may be integral with the optic 13. The optic 13 and the fixation members 15 and 17 may be of any desired configuration, and the configurations illustrated are purely illustrative.

The optic 13 has a central zone 18, inner and outer annular near zones 20 and 22 and annular far zones 24 and 26. In this embodiment, the central zone 18 is circular. The annular zones 20–26 circumscribe the central zone 18, and are concentric and coaxial with the optic 13.

The zones 18–26 are used in describing the vision correction power of the optic 13, and they are arbitrarily defined. Thus, the peripheries of the zones 18–26 and the number of zones may be selected as desired. However to facilitate describing the optic 13, the peripheries of the annular zones 20–26 are considered to be the major zero crossings in FIG. 5. Although the boundaries of the zones 18–26 are indicated by phantom lines in FIG. 1, it should be understood that the optic 13 has no such lines in any of its surfaces and that these lines constitute reference lines which define the zones.

In the embodiment of FIG. 2, the optic 13 has a convex anterior surface 28 and a planar posterior surface 30; however, these configurations are merely illustrative. Although the vision correction power may be placed on either of the surfaces 28 or 30, in this embodiment, the anterior surface 28 is appropriately shaped to provide the desired vision correction powers.

Figure 5:
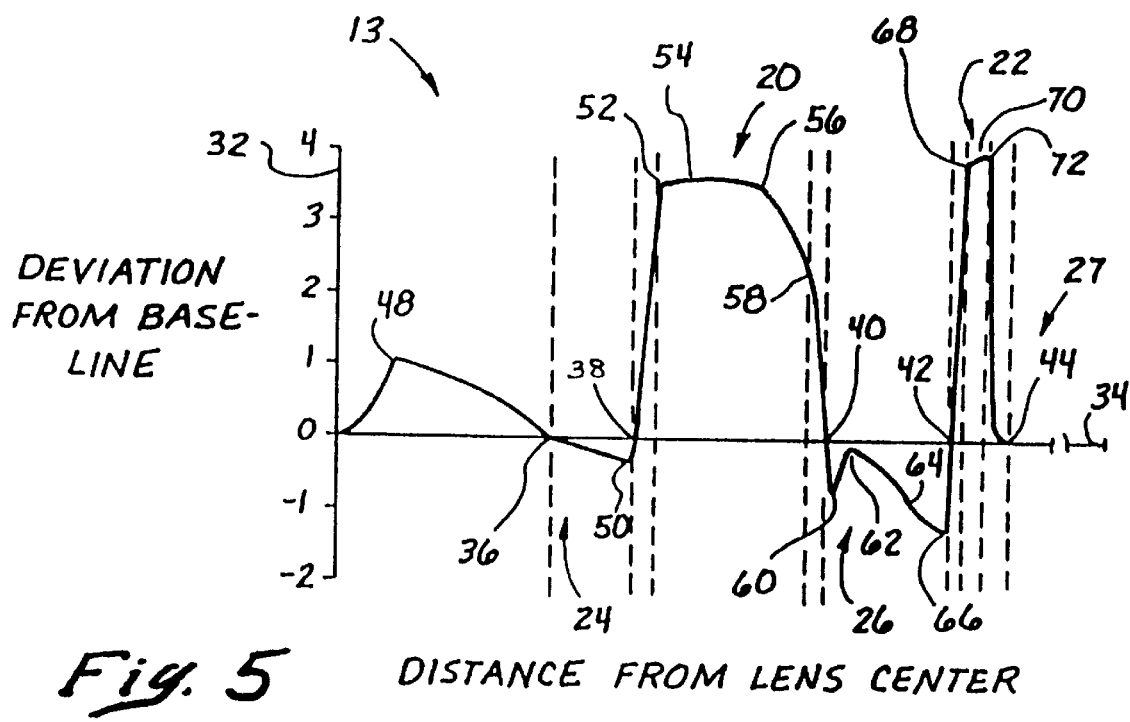
FIG. 5 is a plot of the power of the optic versus distance from the optical axis of the multifocal intraocular lens shown in FIG. 1.

FIG. 5 shows a preferred manner in which the vision correction power of the optic 13 varies from the center or optical axis 32 of the optic to the circular outer periphery 34 of the optic. A preferred power distribution curve for a corneal inlay (corneal inlay lens) may be similar, or identical, to the curve of FIG. 5. In FIG. 5, the vertical or "Y" axis represents the variation in diopter power of the optic 13 from the baseline or far vision correction power, and the "X" or horizontal axis shows the distance outwardly, the radial distance, from the optical axis 32, for example, in millimeters. Thus, the zero-diopter or baseline power of FIG. 5 is the power required for far vision for an IOL. The power variation shown in FIG. 5 is applicable to any radial plane passing through the optic axis 32. In other words, the power at any given radial distance from the optical axis 32 is the same.

The central zone 18 extends from the optical axis 32 to a circular periphery 36, the inner annular far zone 24 is considered as extending from the periphery 36 to a circular periphery 38, inner annular near zone 20 is considered as extending from the periphery 38 to a circular periphery 40, the outer annular far zone 26 is considered as extending from the periphery 40 to the circular periphery 42, and the outer annular near zone 22 is considered as extending from a periphery 42 to a circular periphery 44. The annular zone 27 extends from the periphery 44 radially outwardly to the outer periphery 34 of the optic 13. As shown in FIG. 5, the vision correction power crosses the "X" axis or baseline at the peripheries 36, 38, 40, 42 and 44.

As shown in FIG. 5, the vision correction power varies progressively and continuously from the baseline diopter power at the optical axis 32 to an apex 48 and then decreases continuously and progressively from the apex 48 back to the baseline diopter correction at periphery 36. The apex 48 is closer, in terms of radial distance, to the optical axis 32 than to the periphery 36. As illustrated, apex 48 is located away from the optical axis 32 about 30% of the total radial distance between the optical axis and the circular periphery 36.

The vision correction power then decreases continuously and progressively to a negative diopter power at a periphery 50. The negative diopter power at the periphery 50 is of less power than is required for far vision and may be considered as a far, far vision correction power. From the periphery 50, the vision correction power increases continuously and progressively through the periphery 38 into the inner annular near zone 20. Of course, the diopters shown on the ordinate in FIG. 5 are merely exemplary, and the actual correction provided will vary with the prescription needs of the patient.

Within the inner annular near zone 20, the vision correction power varies continuously and progressively from the periphery 38 to an inner end 52 of a plateau 54. The vision correction power at plateau 54 is considered substantially constant although some variation may occur. The plateau 54 has an outer end 56. At outer end 56, the vision correction power begins a relatively rapid, in terms of diopters changed per unit of radial distance on the optic 13, progressive and continuous decrease to point 58 which has a diopter power equal to about 60% of the average diopter power of plateau 54. The radial width of plateau 54 is equal to about 65% of the radial width, or distance along the Y-axis in FIG. 5, between points 52 and 58. The vision correction power decreases less rapidly (relative to the rate of power decline between points 56 and 58), continuously and progressively from point 58 back to the periphery 40 at the baseline.

With continued reference to FIG. 5, the vision correction power from periphery 40 continuously and progressively decreases to point 60 in far zone 26. From point 60 the vision correction power continuously and progressively increases to apex 62. The vision correction power then decreases to point 64 at which the vision correction power is equal to that at point 60. The vision correction power continues to decrease continuously and progressively to point 66 and then increases continuously and progressively to periphery 42. In far zone 26, apex 62 is located radially closer to point 60 then to point 64. In particular, point 62 is located about 30% of the radial distance from point 60 relative to the total radial distance between points 60 and 64.

In the outer annular near zone 22, the vision correction power increases continuously and progressively from the periphery 42 to the inner end 68 of plateau 70. The vision correction power at plateau 70, which is relatively narrow, increases progressively from inner end 68 to outer end 72 of plateau 70. From the outer end 72, the vision correction power decreases continuously and progressively to periphery 44. The vision correction power remains substantially constant at or about the baseline diopter power from periphery 44 to the periphery 34 of optic 13.

The outer near zone 22 includes plateau 70 with progressively increasing optical powers. These increasing powers in plateau 70, together with the relative narrowness of outer near zone 22 is believed to be effective to diffuse the halo caused by passing light to the outer near zone 22.

By way of comparison and to further illustrate the present invention, FIG. 4 shows the manner in which the vision correction power of a prior art multifocal optic varies from the optical axis of the optic. The zones of the prior art optic in FIG. 4 which correspond to zones of optic 13 in FIG. 5 are identified by the same reference numeral with the addition of the letter "A".

With reference to FIG. 4, the prior art optic, referred to as 13A, has the same baseline diopter power as does optic 13. The central zone 18A extends from the optical axis 32A to a circular periphery 36A. The inner annular far zone 24A is considered as extending from the periphery 26A to the circular periphery 38A, the inner annular near zone 20A is considered as extending from the periphery 38A to the circular periphery 40A. The outer annular far zone 26A is considered as extending from the periphery 40A to the circular periphery 42A and the outer annular near zone 22A is considered as extending from the periphery 42A to a circular periphery 44A. As shown in FIG. 4, the vision correction power includes major crossings of the "X" axis or baseline at the peripheries 36A, 38A, 40A, 42A and 44A. The crossings of the baseline within outer far zone 26A are not considered major.

Regarding the differences between the vision correction power of optic 13 relative to the vision correction power of optic 13A, reference is first made to central zones 18 and 18A. The primary difference between central zones 18 and 18A relates to the positioning of the apexes 48 and 48A. In particular, as noted above, apex 48 is located radially closer to the central axis 32 than to periphery 36. This is contrasted to the positioning of apex 48A which is located closer to the periphery 36A than to the central axis 32A. This difference is believed to is provide optic 13 (and IOL 11) with enhanced performance in viewing near objects, relative to such performance of optic 13A.

Another substantial difference between optic 13 and optic 13A relates to inner annular near zones 20 and 20A. Thus, whereas inner annular near zone 20A of optic 13A includes a plateau 54A which has a substantially constant optical power throughout, plateau 54 is relatively abbreviated and zone 20 includes a region between outer end 56 of plateau 54 and periphery 58 which has a progressively and continuously decreasing optical power. The configuration of inner annular near zone 20 relative to inner annular near zone 20A is believed to reduce the apparent or perceived size of the halo caused by passing light to the near zone 20 relative to the halo caused by passing light to the zone 20A.

A further substantial distinction between optics 13 and 13A relates to the variation in vision correction power in outer far zones 26 and 26A. Thus, whereas zone 26A is only slightly varied in vision correction power relative to the baseline diopter power. The vision correction power in zone 26 includes substantially reduced optical powers, as described previously. The vision correction power of zone 26 is believed to provide increased vision performance in viewing distant objects in dim light or night time relative to the performance obtained with zone 26A.

An additional substantial difference between optic 13 and optic 13A relates to the outer annular near zones 22 and 22A. Specifically, zone 22 is substantially radially more narrow or smaller than is zone 22A. In addition, zone 22A has a relatively wide plateau 70A which includes a substantially constant optical power. In contrast, the plateau 70 of zone 22 includes progressively increasing vision correction powers. Optic 13 with zone 22 diffuses or makes less apparent the halo caused by passing light to zone 22 relative to the halo caused by passing light to zone 22A of optic 13A.

Figure 6:
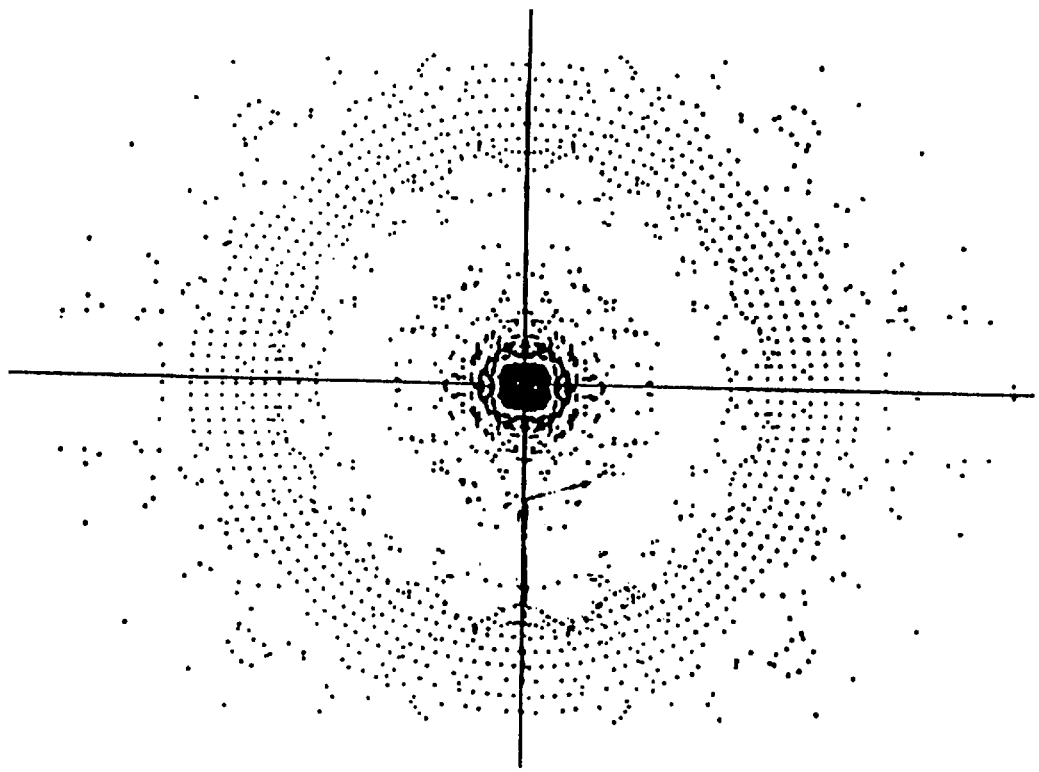
FIG. 6 is a schematic illustration of viewing a distant object during night time conditions using the intraocular lens shown in FIG. 1.
Figure 7:
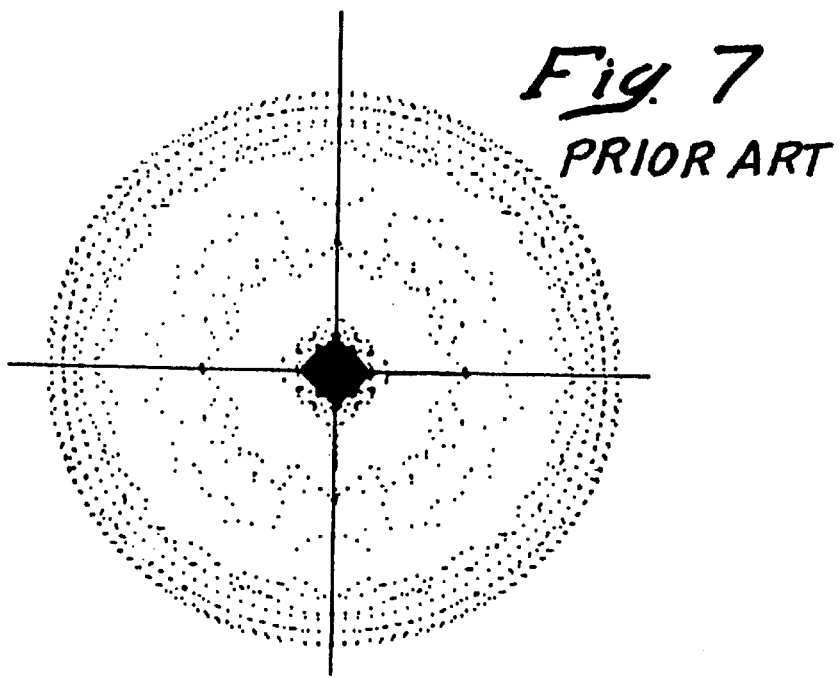
FIG. 7 is a schematic illustration of viewing a distant object during night time conditions using the prior art intraocular lens of FIG. 4.

As a further illustration of the differences between the optic 13 and optic 13A, reference is made to FIGS. 6 and 7 which are schematic illustrations of a distant object viewed during night time conditions using optic 13A and optic 13, respectively.

Referring to FIG. 6, viewing the distant object during night time with optic 13A provides a central image, a halo extending away from the central image and additional random light scattering extending radially beyond the halo.

Referring to FIG. 7, viewing the distant object during night time with optic 13 provides a central image of higher quality than in FIG. 6. In addition, the halo in FIG. 7 extending away from the central image is substantially smaller or reduced in size. Further, substantially no light scattering beyond the halo is apparent radially outwardly from the halo is apparent in FIG. 7. Overall, the image provided by optic 13 (FIG. 7) is superior to the image provided by optic 13A (FIG. 6).

Figure 8:
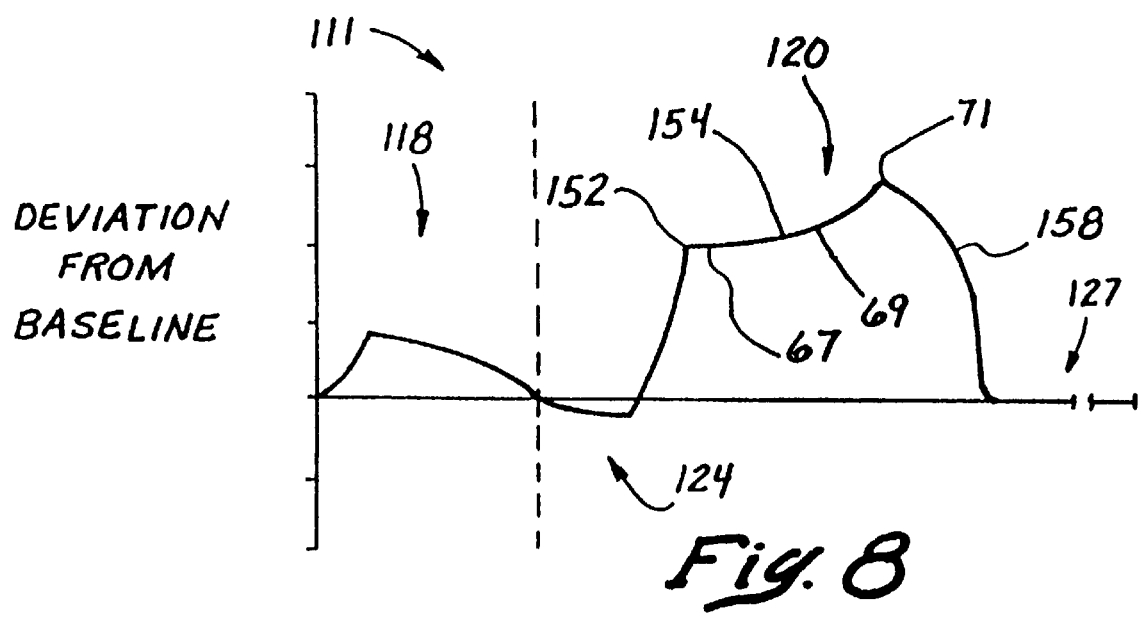
FIG. 8 is a plot of the power of the contact lens shown in FIGS. 3 and 3A versus distance from the optical axis of the lens.

FIGS. 3, 3A and 8 show a contact lens 111 constructed in accordance with the teachings of this invention. The contact lens 111 is sized and configured to be carried or worn on a surface of the eye. Optically, the contact lens 111 may be substantially identical to the optic 13 of FIGS. 1, 2 and 5 in all respects not shown or described herein. Portions of the figures relating to the contact lens 111 which correspond to portions of the figures relating to the intraocular lens 11 are designated by corresponding reference numerals increased by 100.

Optically, the contact lens 111 has a central zone 118, annular near zones 120 and 122, annular far zones 124 and 126 and outer peripheral zone 127 which correspond, respectively, to the zones 18–27 of the intraocular lens 11. In general, the magnitude of the vision correction powers, relative to the baseline diopter power, is reduced in the contact lens 111 relative to the magnitude of the vision correction powers in the optic 13 of IOL 11. The contact lens 111 has a convex anterior surface 128 and a posterior surface 130 which is concave and configured to the desired shape of the eye of the wearer. Of course, the corrective powers could be provided on the posterior surface 130, if desired.

Optically, the contact lens 111 is very similar to the optic 13 of intraocular lens 11. The primary difference between the optic 13 and the contact lens 111 relates to the configuration of the inner near zone 120.

Specifically, with reference to FIG. 8, inner near zone 120 includes a plateau 154 having an inner end 152 and an inner region 68 which has a substantially constant vision correction power. However, the region 70 of plateau 154 extending radially outwardly from inner region 68 includes vision correction powers which increase continuously and progressively to apex 72. The vision correction power radially outwardly from apex 72 decreases continuously and progressively to point 158. Thereafter, the vision correction power decreases continuously and progressively toward the baseline diopter power.

The vision correction power at point 158 is approximately 60% of the vision correction power at the apex 72. In addition, the apex 72 is located away from inner end 152 about 70% of the total radial distance between point 152 and point 158. The above-noted configuration of inner near zone 120 reduces the size of the halo caused by passing light to zone 120 relative to the halo caused by passing light to a similar inner near zone which has a substantially constant vision correction power across the entire distance from point 152 to point 158.

Figure 9:
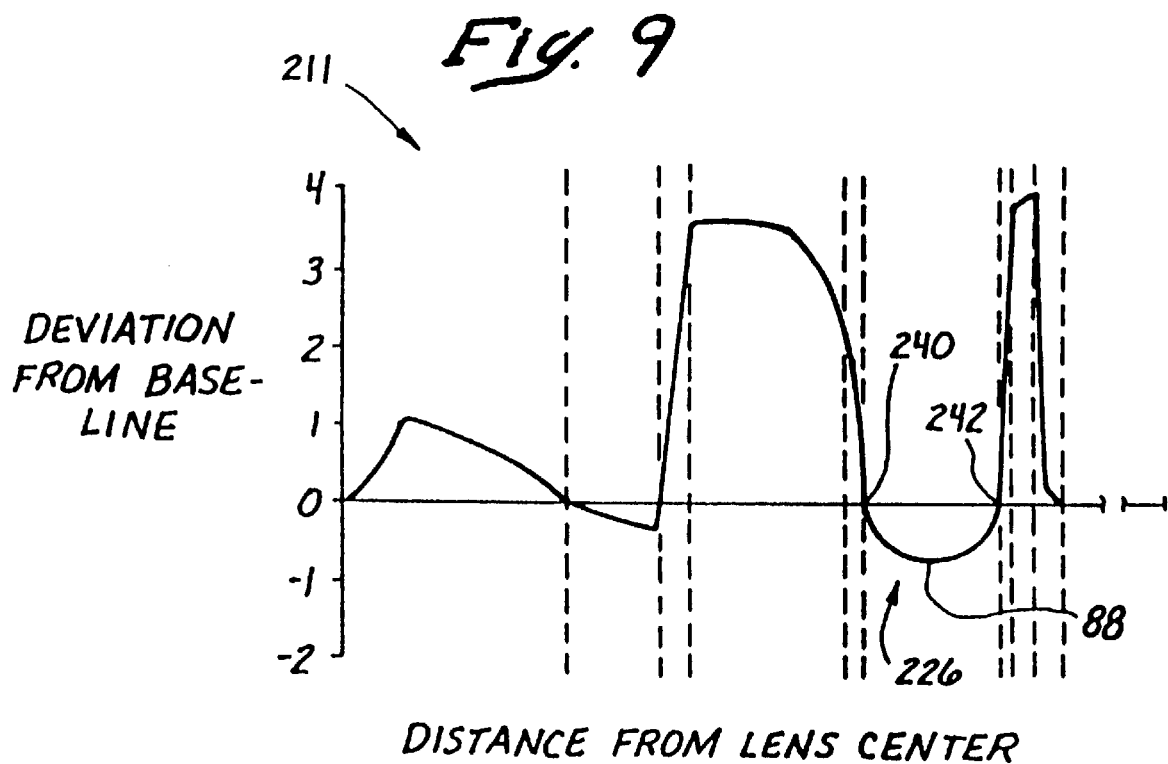
FIG. 9 is a plot of the power of an optic of an alternate intraocular lens in accordance with the present invention versus distance from the optical axis of the optics.

FIG. 9 shows an alternate IOL 211 constructed in accordance with the teachings of the present invention. Except as expressly described herein, IOL 211 is similar to IOL 11. Portions of IOL 211 which correspond to portions of IOL 11 are designated by the corresponding reference numerals increased by 200.

With reference to FIG. 9, the major difference between IOL 11 and IOL 211 relates to the configuration of outer far zone 226. Specifically, outer far zone 226 begins at circular periphery 240 and decreases continuously and progressively to apex 88 which is located substantially equal radial distances from periphery 240 and circular periphery 242. From apex 88, the vision correction power increases continuously and progressively to the periphery 242.

Outer far zone 226 is effective to enhance the performance characteristics of the lens when viewing a distant object in dim light or at night time. In addition, outer far zone 226, or an outer far zone configured similarly to outer far zone 226 can be included in place of either outer far zone 26 in optic 13 of intraocular lens 11 or in place of an outer far zone of a contact lens, such as outer far zone 126 of contact lens 111.

The present multifocal ophthalmic lenses provide substantial benefits, such as image quality when viewing a distant object in dim light or night time. The present lenses mitigate against the halos which are apparent or perceived as a result of causing light to pass to the outer near zone or zones of such lenses, relative to lenses including an outer near zone or zones which have substantially constant vision correction powers. Moreover, the present enhanced lenses can be cost effectively produced using conventional and well known techniques. Thus, the present lenses provide substantial benefits with few or no significant adverse effects.

While this invention has been described with respect to various specific examples and embodiments, it is to be understood that the invention is not limited thereto and that it can be variously practiced within the scope of the following claims.

What is claimed is:

1. An intraocular lens having a baseline diopter power for far vision correction, the intraocular lens comprising:
   a near zone including an inner region having a substantially constant vision correction power greater than the baseline diopter power; and
   an additional near zone located outwardly of the near zone and having vision correction powers greater than the baseline diopter power and the near zone, wherein the near zone and the additional zone each has a radial width and the radial width of the additional near zone is less than about 40% of the radial width of the near zone.

2. The intraocular lens of claim 1 wherein the near zone is annular, and which further comprises a central zone having a vision correction power greater than the baseline diopter power, the near zone circumscribes the central zone.

3. The intraocular lens of claim 1 wherein the additional near zone includes a central plateau region having an inner end and an outer end and vision correction powers which increase progressively from the inner end to the outer end.

4. The intraocular lens of claim 3 wherein the additional near zone includes vision correction powers which diffuse a halo caused by passing light to the additional near zone relative to the halo caused by passing light to a similar additional near zone of a substantially identical lens in which the similar additional near zone has a constant vision correction power throughout.

5. The intraocular lens of claim 1 wherein the near zone and the additional near zone are annular and the additional near zone circumscribes the near zone.

6. An intraocular lens having a baseline diopter power for far vision correction, the intraocular lens comprising:
   a near zone including an inner region having a substantially constant vision correction power greater than the baseline diopter power; and
   an additional near zone located outwardly of the near zone and having vision correction powers greater than the baseline diopter power and the near zone and including a central plateau region having an inner end and an outer end and vision correction powers which increase progressively from the inner end to the outer end.

7. The intraocular lens of claim 6 wherein the additional near zone includes vision correction powers which diffuse a halo caused by passing light to the additional near zone relative to the halo caused by passing light to a similar additional near zone of a substantially identical lens in which the similar additional near zone has a constant vision correction power throughout.

8. The intraocular lens of claim 6 wherein the near zone is annular, and which further comprises a central zone having a vision correction power greater than the baseline diopter power, the near zone circumscribes the central zone.

9. The ophthalmic lens of claim 6 wherein the near zone and the additional near zone are annular and the additional near zone circumscribes the near zone.

10. The intraocular lens of claim 6 wherein the near zone and the additional near zone each has a radial width and the radial width of the additional near zone is less than the radial width in the near zone.

* * * * *